US011220786B2

(12) United States Patent
Kallerdahl et al.

(10) Patent No.: US 11,220,786 B2
(45) Date of Patent: Jan. 11, 2022

(54) METHOD AND DEVICE FOR MEASURING PROPERTY OF MOVING FIBER WEB

(71) Applicant: Valmet Technologies Oy, Espoo (FI)

(72) Inventors: Tommy Kallerdahl, Espoo (FI); Johnny Ånerud, Espoo (FI)

(73) Assignee: Valmet Technologies Oy, Espoo (FI)

( * ) Notice: Subject to any disclaimer, the term of this patent is extended or adjusted under 35 U.S.C. 154(b) by 0 days.

(21) Appl. No.: 16/803,596

(22) Filed: Feb. 27, 2020

(65) Prior Publication Data

US 2020/0277734 A1    Sep. 3, 2020

(30) Foreign Application Priority Data

Feb. 28, 2019  (EP) ..................................... 19159984

(51) Int. Cl.
*D21F 7/00* (2006.01)
*D21G 9/00* (2006.01)
*G01N 22/04* (2006.01)

(52) U.S. Cl.
CPC ............ *D21F 7/00* (2013.01); *D21G 9/0009* (2013.01); *G01N 22/04* (2013.01)

(58) Field of Classification Search
USPC ................................................. 162/198, 263
See application file for complete search history.

(56) References Cited

U.S. PATENT DOCUMENTS

| 4,735,087 A | 4/1988 | Hourani et al. |
| 6,567,720 B1 | 5/2003 | Figiel |

OTHER PUBLICATIONS

Partial European Search Report, with accompanying Provisional Opinion dated Apr. 20, 2020, for EP20159450.

*Primary Examiner* — Mark Halpern
(74) *Attorney, Agent, or Firm* — Stiennon & Stiennon

(57) ABSTRACT

A traversable measuring device (15) for determining a cross direction profile of a property of a moving lignocellulose-containing fiber web (2). The measuring device has a property measuring sensor (23) for determining a measurement result representing the property of the web at multiple cross directional measurement positions (P1, P2, P3, P4), a position measuring sensor (24) for determining the cross directional measurement position of the property measuring sensor associating to the respective measurement result, and an analysis device (25) for receiving the measurement results and the respective cross directional measurement positions (P1, P2, P3, P4) and for allocating the measurement results with the respective cross directional measurement positions for forming the cross direction profile of the web property (2). The measuring device has a mounting bracket (16) that is detachably fixable with quick clamping for fastening the measuring device at a measurement site in a fiber web machine (1).

17 Claims, 5 Drawing Sheets

METHOD AND DEVICE FOR MEASURING PROPERTY OF MOVING FIBER WEB

CROSS REFERENCES TO RELATED APPLICATIONS

This application claims priority on EP 19159984, filed Feb. 28, 2019, the disclosure of which is incorporated by reference herein.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The present invention relates to a method for determining a cross direction profile of a property of a moving lignocellulose-containing fiber web in a fiber web machine.

The present invention relates also to a device for determining a cross direction profile of a property of a moving lignocellulose-containing fiber web in a fiber web machine.

One of the most complex parts of a manufacturing chain of a tissue web is a drying section of a tissue machine. The drying section of the tissue machine comprises a Yankee cylinder that is used for drying the tissue web to be manufactured. The Yankee cylinder comprises a heated outer surface against which the tissue web to be manufactured is brought for drying the web. In a direction of a motion of the tissue web the Yankee cylinder is preceded by a counter roll that presses the moving tissue web against the outer surface of the Yankee cylinder. The drying section of the tissue web comprises typically also at least one hood for blowing heated air against the tissue web supported to the outer surface of the Yankee cylinder, the hood being located above the Yankee, i.e. after a nip formed between the counter roll and the Yankee cylinder in the direction of the motion of the tissue web.

A moisture of the moving tissue web is one property of the moving tissue web as a point of interest in the manufacturing of the tissue web. A cross direction moisture profile of the moving tissue web especially at a location right after the nip between the counter roll and the Yankee cylinder before the tissue web enters into an area of an influence of the hood and sets a condition for a drying performance to be provided by at least one of the counter roll, the Yankee cylinder and the hood. An unequal cross direction moisture profile of the moving tissue web should be equalized by controlling the operation of the at least one of the counter roll, Yankee cylinder and hood for avoiding operational problems in a post processing of the tissue web in a converting section of the tissue machine, including for example at least one of slitting, layering, perforation and/or surface texturing of the tissue web.

Presently the cross-direction moisture profile of the moving tissue web at the location right after the nip between the counter roll and the Yankee cylinder before the tissue web enters into the influence area of the hood is determined by taking physical samples of the moving tissue web from the Yankee cylinder surface by manual means. This is called a scraping of the sample. The wet weight of the carefully preserved sample is determined, the sample is dried in a heated oven for a certain period of time, such as 12 to 24 hours, until all water is vaporized away from the sample, and then its dry weight is determined. The moisture content of the sample may then be determined by the wet weight and the dry weight of the sample. When this procedure is carried out for a number of samples scraped at different positions in the cross direction of the tissue web, the cross-direction moisture profile of the tissue web is obtained.

One disadvantage of this method to determine the cross-direction moisture profile of the tissue web is it takes a very long time, even more than 24 hours, so in fact the moisture profile thus obtained is the profile from yesterday and efforts to affect it may be incorrect for today's operational condition of the tissue machine. Another disadvantage is a need to use a manually operated mechanical tool to scrape the samples from the tissue web supported on the Yankee cylinder surface, which is unsafe for a person taking the sample because he/she has to approach closely to the machine section operating with a high speed and at elevated temperatures. The scraping of the physical samples from the moving tissue web also breaks the uniform structure of the moving tissue web and thus leads to a loss of production of the tissue web produced during the sampling.

SUMMARY OF THE INVENTION

An object of the present invention is to provide a novel method and device for determining a cross direction profile of a property of a moving lignocellulose-containing fiber web in a fiber web machine.

The invention is a measuring device having a mounting bracket that is detachably fixable with quick clamping for fastening the measuring device at a measurement site in the fiber web machine. The invention is further a method for determining a measurement result representing the property of the web at a number of cross directional measurement positions in a direction of motion of the web at a location after the counter roll wherein the web is supported against the Yankee cylinder, determining a measurement position associating to the respective measurement result of the property of the moving fiber web in the cross direction of the web band allocating the measurement results of the property of the moving fiber web with the respective cross directional measurement positions for forming the cross-direction profile of the property of the moving fiber web.

The invention is based on the idea of determining a cross direction profile of a property of a moving fiber web with a measuring device that is traversable in the cross direction of the moving fiber web but easily movable to a desired measurement site at a fiber web machine. The measuring device comprises a property measuring sensor movable in a cross direction of the moving fiber web and configured to determine a measurement result representing the property of the web at a number of cross directional measurement positions in response to a movement of the property measuring sensor in the cross direction of the moving fiber web, a position measuring sensor configured to determine a measurement position of the property measuring sensor associating to the respective measurement result of the property of the moving fiber web in the cross direction of the web, and an analysis device for receiving the measurement results representing the property of the moving fiber web and the respective measurement positions and for allocating the measurement results of the property of the moving fiber web with the respective cross directional measurement positions of the property measuring sensor for forming the cross direction profile of the property of the moving fiber web. The measuring device further comprises a mounting bracket that is detachably fixable with quick clamping for fastening the measuring device at a desired measurement site in the fiber web machine.

An advantage of the invention is that the measuring device disclosed is traversable across the web and thanks to the quick clamping may be moved from one measurement location to another measurement location, whereby it may be located in the fiber web machine at the desired location where a property of the moving lignocellulose-containing fiber web is intended to be temporarily measured. The measuring device allows measurement of the properties of the moving fiber web in locations or places in the fiber web machine where it is very difficult or unsafe or unprofitable to organize the measurement operation in another way.

BRIEF DESCRIPTION OF THE DRAWINGS

In the following the invention will be described in greater detail by means of preferred embodiments with reference to the accompanying drawings, in which.

For the sake of clarity, the figures show some embodiments of the invention in a simplified manner. Like reference numerals identify like elements in the figures.

DESCRIPTION OF THE PREFERRED EMBODIMENTS

Figure 1:
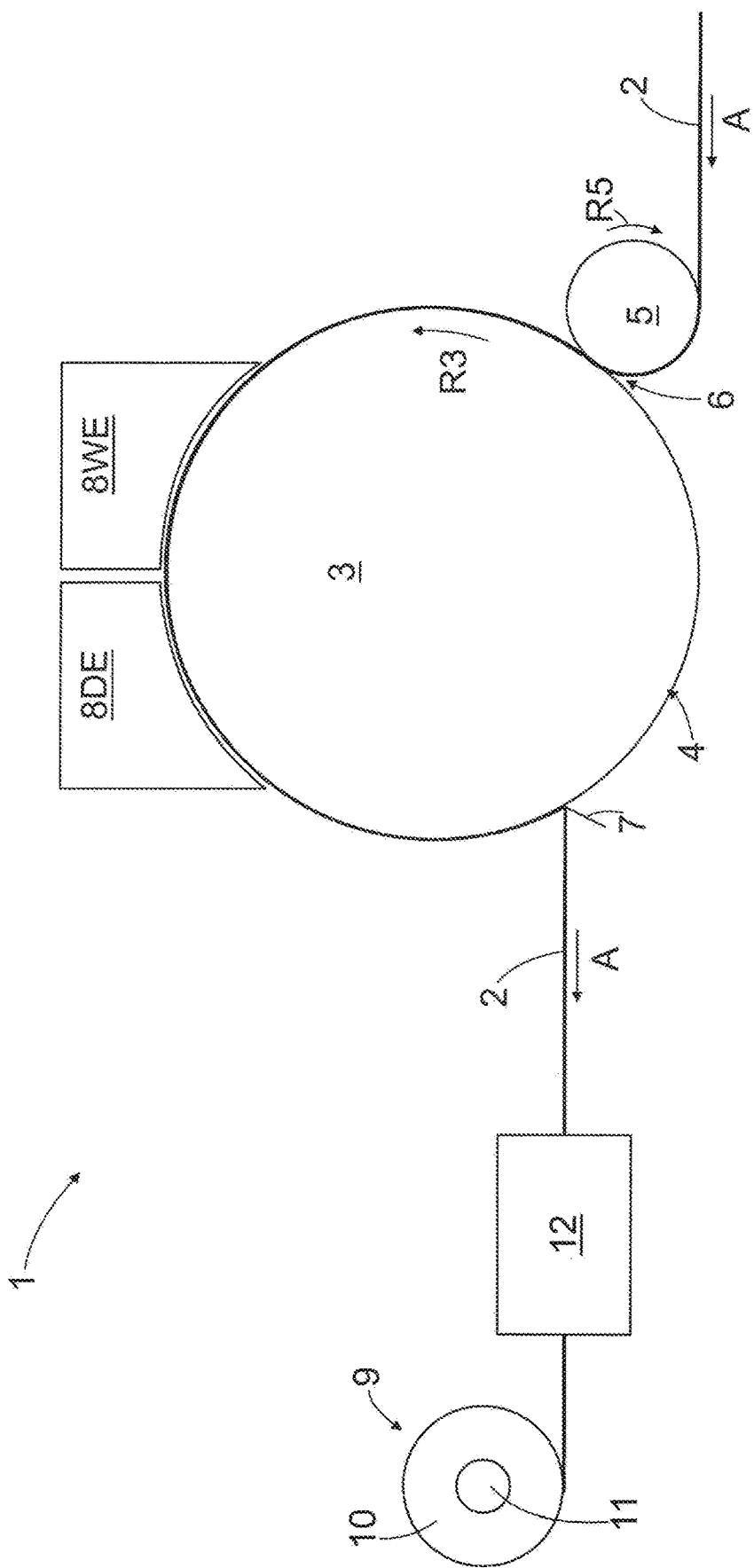
FIG. 1 shows schematically a side view of a part of a tissue machine and a Yankee cylinder therein.

FIG. 1 shows schematically a side view of a part of a tissue machine 1. The tissue machine 1 comprises a headbox (not shown) for receiving fiber suspension or slush pulp from a pulping process (not shown) preceding the headbox. The headbox supplies the fiber suspension to a wire section (not shown) wherein a tissue web 2 is formed of the fiber suspension. For the sake of clarity, the pulping process, the headbox, the wire section and any possible devices therein are not disclosed in the figures, but their general structures and operations are known for a person skilled in the art. The direction of the travel of the tissue web 2 in FIG. 1 is from right to left and shown with an arrow indicated with a reference sign A.

From the wire section the tissue web 2 is forwarded to a Yankee cylinder station for drying the tissue web 2, the Yankee cylinder station providing at least a part of a drying section of the tissue machine 1. The Yankee cylinder station comprises a Yankee cylinder 3 the rotation direction of which is shown with an arrow indicated with a reference sign R3. The Yankee cylinder 3 is a large diameter cylinder filled with hot steam that heats an outer surface 4 or a cylindrical surface 4 of the Yankee cylinder 3.

The tissue web 2 is pressed against the hot outer surface 4 of the Yankee cylinder 3 with a counter roll 5 and a press felt (not shown) travelling via the roll 5 at a nip 6 formed between the opposing Yankee cylinder 3 and counter roll 5. The counter roll 5 can be a suction roll, a press roll with grooved or un-grooved surface, a shoe roll or other type of an extended nip roll. Some water may be removed from the tissue web 2 due to the pressure in the nip 6 and/or a suction effect provided by the counter roll 5. The rotation direction of the roll 5 is shown with an arrow indicated with a reference sign R5.

After the nip 6 the press felt overlying the tissue web 2 is separated from the tissue web 2 and the tissue web 2 is attached to the hot outer surface 4 of the Yankee cylinder 3. The hot outer surface 4 evaporates water from the tissue web 2, thereby drying the tissue web 2 further by removing from the tissue web 2 water still remaining in the web 2. Any condensation water that may arise inside the Yankee cylinder 3 is removed from the cylinder 3. The tissue web 2 attached to the outer surface 4 of the Yankee cylinder 3 and travelling with the outer surface 4 of the cylinder 3 is detached from the Yankee cylinder 3 with a doctor blade 7, also called a creping doctor 7.

The Yankee cylinder station may also comprise one or more hoods laid above the Yankee cylinder 3 next to the outer surface 4 of the cylinder 3 for blowing heated air against the tissue web 2. In FIG. 1 there is a wet end side hood 8WE and a dry end side hood 8DE, the wet end side hood 8WE being the closest hood relative to the counter roll 5 in the direction of the travel or motion of the tissue web 2. By the hood(s) a moisture profile of the tissue web 2 may be affected on the web in a cross direction of the web 2.

From the Yankee cylinder 3 the tissue web 2 is forwarded to the pope reel 9, where it is guided by a reeling drum (not shown) and rolled up on a reel spool 11 to form a tissue parent roll 10.

A cross direction moisture profile of the moving tissue web 2 after the nip 6 between the counter roll 5 and the Yankee cylinder 3 but before the tissue web 2 enters into an area of an influence of the wet end side hood 8WE sets a condition for a drying performance of at least one of the counter roll 5, the Yankee cylinder 3 and the at least one hood 8WE, 8DE. An unequal cross direction moisture profile of the moving tissue web 2 should be equalized by controlling the operation of at least one of the counter roll 5, Yankee cylinder 3 and at least one hood 8WE, 8DE for avoiding operational problems in post processing of the tissue web 2 in a converting section of the tissue machine 1. For example, linear load of the counter roll 5 at the nip 6, blow velocity of the hoods 8WE, 8DE, condensate removal from the Yankee cylinder 3 and other cross-machine adjustable controls are among those control methods by which the cross-profile uniformity of the tissue web 2 can be adjusted. The converting section is shown in FIG. 1 very schematically by a box indicated with reference sign 12. The converting section 12 may include for example at least one of slitting, layering, perforation and/or surface texturing of the tissue web 2.

It has been found out that a temperature of the moving tissue web 2 in the movement direction A of the tissue web 2 after the nip 6, wherein the tissue web 2 is already supported against the outer surface 4 of the Yankee cylinder 3 but has not yet entered into the area of the influence of the at least one hood 8WE, 8DE, is directly proportional to a dryness of the moving tissue web 2. The dryness of the moving tissue web 2 being a property of the moving tissue web 2 that directly indicates the moisture of the moving tissue web 2. The temperature of the moving tissue web 2 being directly proportional to the dryness of the moving tissue web 2 thus means that the higher the temperature of the moving tissue web 2, the higher the dryness of the moving tissue web 2, and consequently, the lower the moisture of the moving tissue web 2. This has been shown in FIGS. 2a and 2b, wherein it has been disclosed cross direction temperature and dryness profiles of the moving tissue web 2 obtained as a result of two different comparison measurement tests between the temperature and the dryness of the moving tissue web 2 right after a nip 6 in a tissue machine 1 before the tissue web 2 enters into the influence area of the at least one hood 8WE, 8DE. In the measurement tests of FIGS. 2a, 2b the temperature of the moving tissue web 2 has been measured by a pyrometer measuring infrared radiation radiating from the moving tissue web 2 when the web 2 has been supported against an outer surface of a Yankee cylinder 3. The dryness of the moving tissue web 2 has been determined by scraping samples off the moving tissue web 2 and weighing and drying them in the way disclosed above in the section "Background of the invention". The comparison measurements tests were carried out in three different cross direction positions of the moving tissue web 2, i.e. positions "P1", "P2" and "P3" indicated in FIGS. 2a, 2b. The comparison measurements tests were carried out in the same tissue machine but on different days.

Figure 2A:
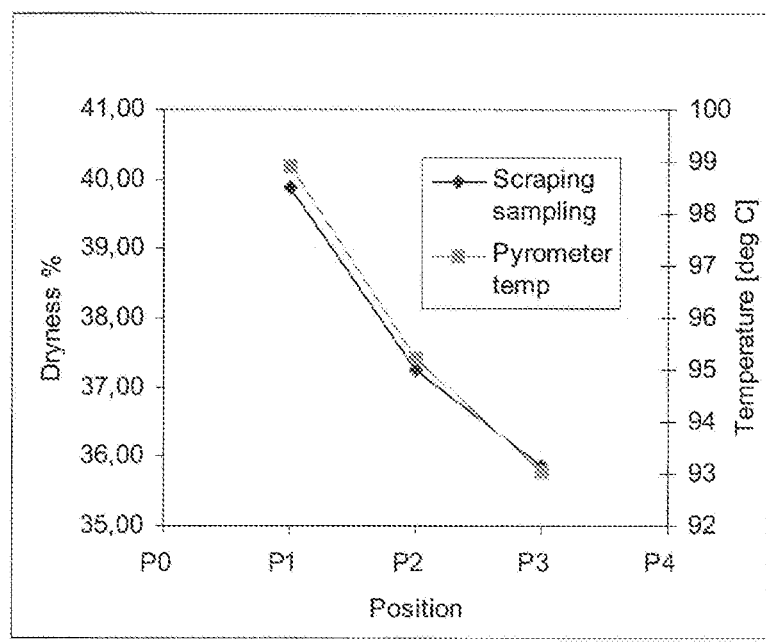
FIG. 2a shows schematically first comparison measurement tests between temperature and dryness of a moving tissue web.
Figure 2B:
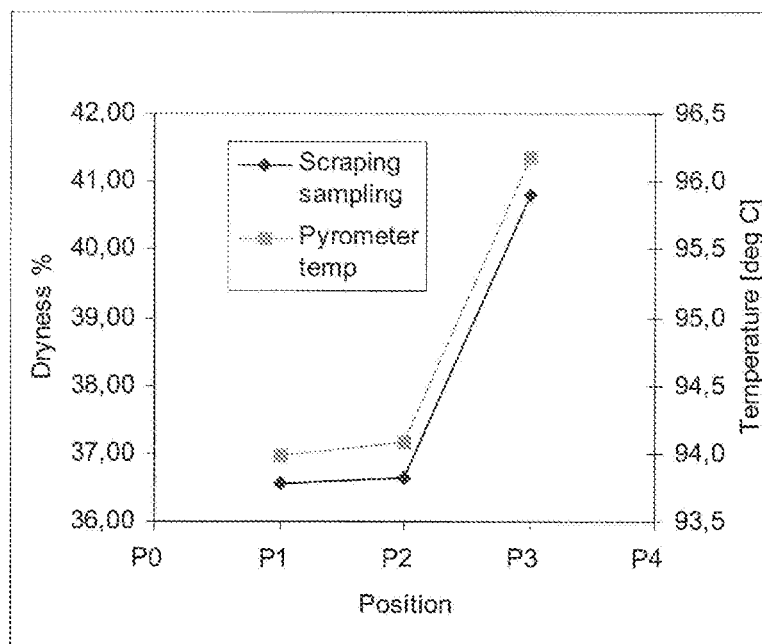
FIG. 2b shows schematically second comparison measurement tests between temperature and dryness of a moving tissue web.

On the basis of FIGS. 2a and 2b it can be verified that the temperature of the moving tissue web 2 after the nip 6 is directly or at least substantially directly proportional to the dryness of the moving tissue web 2 right after the nip 6, whereby the temperature of the moving tissue web 2 can be used as an indicator of the moisture of the moving tissue web 2. It may be emphasized herein that the temperature of the moving tissue web 2 does not indicate the absolute value of the dryness or moisture of the moving tissue web 2. The absolute value of the dryness or moisture of the moving tissue web 2 would need a correlation factor that describes the exact proportionality between the temperature and the dryness or moisture of the moving tissue web 2, which correlation factor must separately be determined for each tissue machine and for each operating condition thereof. However, as long as only a shape—most often the uniformity—of the cross direction profile of the dryness or moisture of the moving tissue web is of interest, while absolute or exact values of the dryness or moisture are not of interest, it is sufficient to use the shape of the cross direction profile of the temperature to represent the shape of the cross direction profile of the dryness or moisture of the moving tissue web 2.

Figure 3:
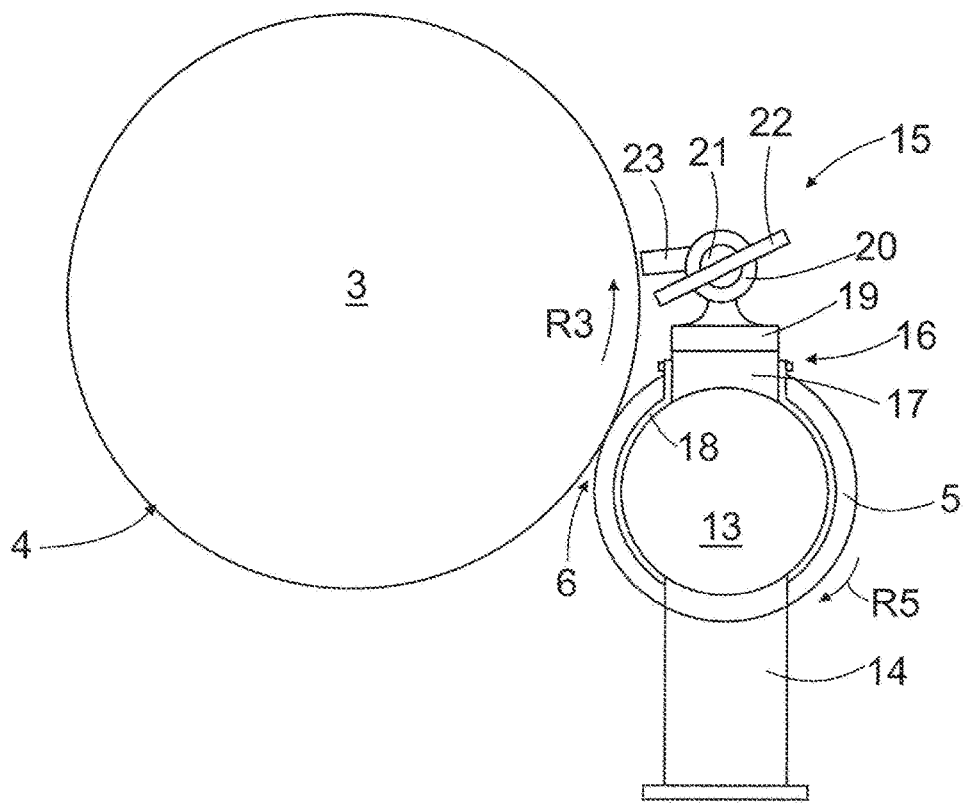
FIG. 3 shows schematically an end view of a Yankee cylinder, a counter roll and a measuring device for measuring a cross direction temperature profile of a moving tissue web.
Figure 4:
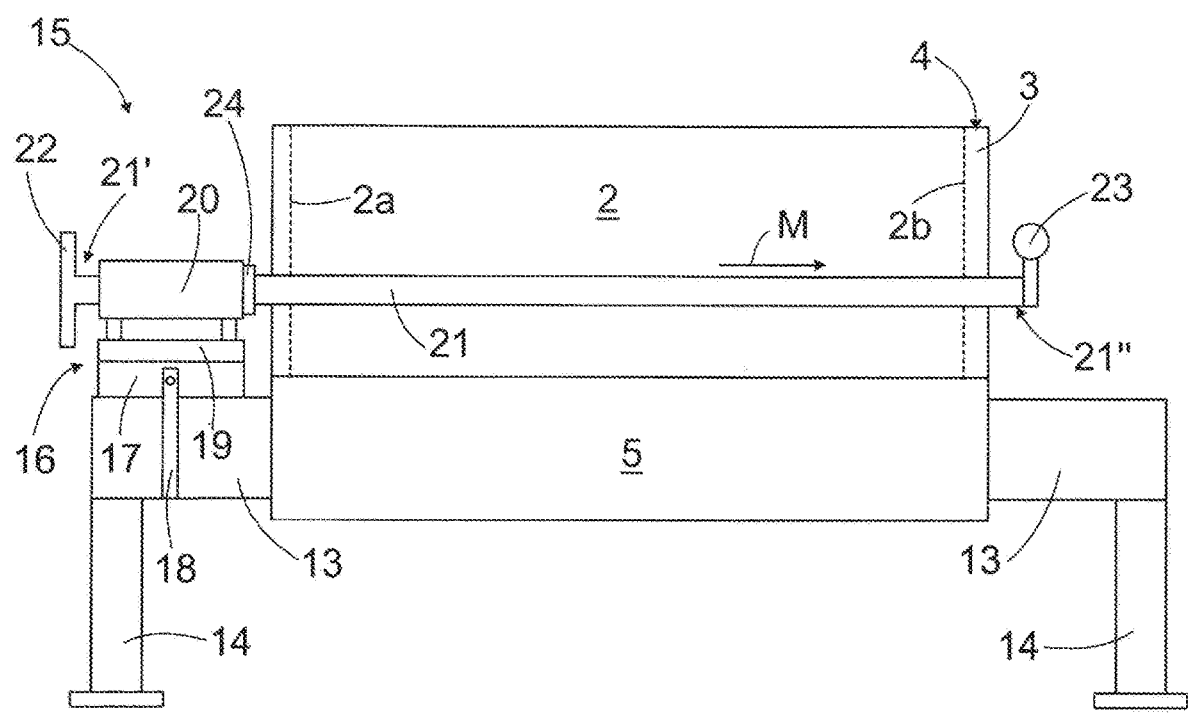
FIG. 4 shows schematically a front view of the Yankee cylinder, the counter roll and the measuring device shown in FIG. 3.
Figure 5:
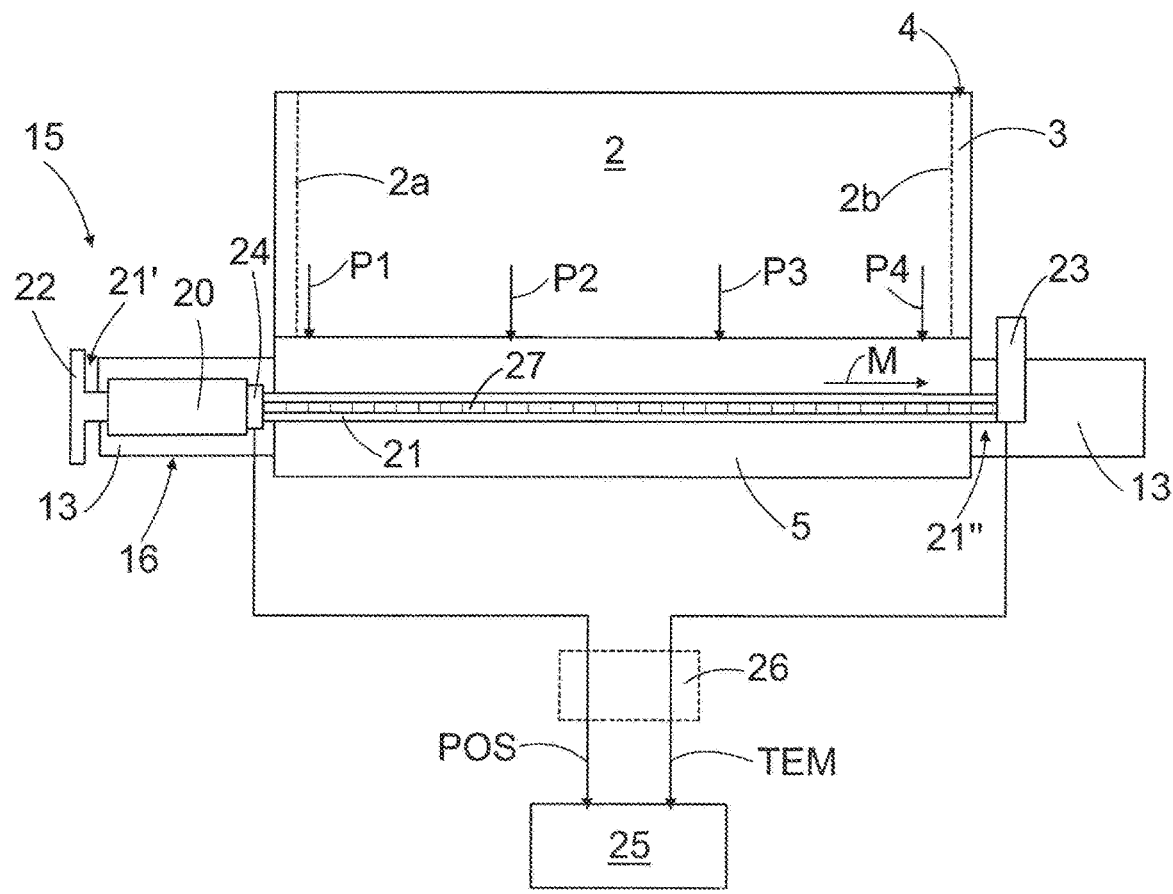
FIG. 5 shows schematically a top view of the Yankee cylinder, the counter roll and the measuring device shown in FIG. 3.

FIG. 3 shows schematically an end view of a Yankee cylinder 3, a counter roll 5 and a measuring device 15 for measuring a cross direction temperature profile of a moving tissue web 2. FIG. 4 shows schematically a front view of the Yankee cylinder 3, the counter roll 5 and the measuring device 15 shown in FIG. 3 and FIG. 5 shows schematically an upper view of the Yankee cylinder 3, the counter roll 5 and the measuring device 15 shown in FIG. 3. A front edge 2a and a rear edge 2b of the moving tissue web 2 are indicated in FIGS. 4 and 5 with broken lines. In the example of FIGS. 3 to 5, and later in the example of FIG. 6, it is thus assumed that the property of the moving tissue web 2 to be measured is the temperature of the moving tissue web 2 whereby the measuring device 15 is used for measuring the cross-direction temperature profile of the moving tissue web 2. The measuring device 15 according to the solution disclosed herein may, however, be also configured to be used for measuring some other property of the moving tissue web 2 as well.

As shown in FIG. 5 the measuring device 15 comprises a mounting bracket 16 which is preferably arranged to allow instant clamping and dismounting, i.e. quick clamping, so that the device is simple and easy to use for temporary measurements or measurements in various positions, i.e. measurement sites, in the machine 1. The quick clamping allows the mounting bracket 16 to be removably fastened to the counterpart at the measurement site without using any tools. The mounting bracket 16 is fastened to a suitable counterpart in the tissue machine 1, the counterpart thus forming an intended fastening point for the measuring device 15 in the tissue machine 1. When the temperature of the moving tissue web 2 is to be measured right after the nip 6 at a location where the moving tissue web 2 is supported on the outer surface 4 of the Yankee cylinder 3 but before the tissue web 2 enters the influence area of the wet end side hood 8WE, the fastening point for the measuring device 15 may be provided by a counter roll bearing housing cover 13 that is supported in place by an appropriate pedestal 14. Alternatively, the counterpart forming the fastening point for the measuring device 15 may be provided by a special-purpose carriage, for example, if there is no available suitable fastening point for the measuring device 15 at the intended measurement site in the machine.

As shown in FIG. 4 the mounting bracket 16 of the measuring device 15 comprises a mounting frame 17 that is to be fastened to the counter roll bearing housing cover 13. The mounting frame 17 may be a magnetic part as such or it may comprise a magnetic part or portion so that the mounting frame 17 may be fastened to the counter roll bearing housing cover 13 by at least a magnetic force generated between the mounting frame 17 and the counter roll bearing housing cover 13. The fastening of the mounting frame 17 to the counter roll bearing housing cover 13 may further be secured by at least one fastening strap 18 arranged around the counter roll bearing housing cover 13 and fastened to the opposite sides of the mounting frame 17. The mounting frame 17 is thus removably fastened or detachably fixable to the fastening point intended for the measuring device 15. A shape of the mounting bracket 16, especially a shape of a surface of the mounting frame 17 intended to be set opposite to the counter roll bearing housing cover 13, may be configured to substantially correspond to a shape of the counter roll bearing housing cover 13 in order to increase a stability of the fastening of the mounting bracket 16 to the counter roll bearing housing cover 13.

The mounting bracket 16 further comprises a support stand 19 on top of the mounting frame 17 and being fastened to the mounting frame 17. Preferably the support stand 19 is fastened removably to the mounting frame 17 by bolts, for example, whereby the mounting frame 17 and the support stand 19 may be handled separately, thus decreasing the weight of parts to be handled at a time.

The support stand 19 comprises a substantially horizontally aligned supporter 20 that is directed in the cross direction of the moving tissue web 2 but not intended to extend up to the area of the moving tissue web 2 in the tissue machine 1. The supporter 20 of FIGS. 3 to 5 is a hollow cylindrical element intended to receive an actuating member 21 and provide a support for the actuating member 21 that is arranged to run through the supporter 20 such that the actuating member 21 may be moved relative to the supporter 20 back and forth through the supporter 20 over the moving tissue web 2 in the cross direction and at a distance from the moving tissue web 2. In other words, the actuating member 21 may thus be traversed relative to the supporter 20 back and forth in the cross direction of the moving tissue web 2. The actuating member 21 may be supported to the supporter 20 for example by ball bearing bushings arranged at the ends of the supporter 20.

The actuating member 21 of FIGS. 3 to 5 is an elongated rod which has a first end 21' intended to remain on the side of the support stand 19 facing away from the moving tissue web 2 and a second end 21" intended to remain on the side of the support stand 19 facing to the moving tissue web 2. The first end 21' of the actuating member 21 is provided with a handhold element 22 at which a person operating the measuring device 15 may grip in order to move the actuating member 21 back and forth over the tissue web 2 in the cross direction of the web 2. At the second end 21" of the actuating member 21 there is a temperature measuring sensor 23 for measuring the temperature of the moving tissue web 2, the temperature measuring sensor 23 remaining at a distance from the surface of the moving tissue web 2. When the person operating the measuring device 15 moves the actuating member 21 across the moving tissue web 2, the temperature measuring sensor 23 moves with the actuating member 21 over the moving tissue web 2 in the cross direction thereof and measures the temperature of the web 2 at different cross-directional measurement positions P1, P2, P3, P4 for obtaining the cross direction temperature profile of the moving tissue web 2.

According to an embodiment the mounting bracket 16 comprises at least one fastening strap 18 for fastening the mounting bracket 16 to the counterpart forming the fastening point for the mounting bracket 16, whereby a clamping force is generated by the at least one fastening strap 18 between the mounting bracket 16 and the counterpart forming the fastening point for the mounting bracket 16 at the measurement site. According to this embodiment the mounting bracket 16 may be fastened to the counterpart only by the at least one fastening strap 18, whereby the mounting bracket 16 or the mounting frame 17 thereof does not necessarily comprise any magnetic part or portion as disclosed above. The mounting bracket 16, the mounting frame 17 and/or the at least one fastening strap 18 may comprise tensioning devices or tensioners by which a suitable clamping force may be generated between the mounting bracket 16 or the mounting frame 17 and the at least one fastening strap 18.

According to an embodiment the mounting bracket 16 comprises a mounting frame 17 and at least one fastening strap 18 to be arranged around the counterpart for the measuring device 15 and fastened to opposite sides of the mounting frame 17 so as to fasten the mounting frame 17 to the counterpart by the clamping force generated by the at least one fastening strap 18 between the mounting frame 17 and the counterpart. Furthermore, the support stand 19 is fastened preferably detachably to the mounting frame 17 and comprises a supporter 20 configured to receive the actuating member 21 such that the actuating member 21 is movable relative to the supporter 20 as controlled by a controlling element such as the handhold element 22.

Thus, the mounting bracket 16 may comprise, for fastening the mounting bracket 16 to a counterpart forming the fastening point for the mounting bracket 16 at the measurement site, at least one of at least one magnetic part/portion and at least one fastening strap 18 for fastening the mounting bracket 16 to the counterpart by at least one of magnetic force and clamping force. The mounting bracket 16 or at least the mounting frame 17 thereof may thus be removably fastened to the counterpart with quick clamping, allowing clamping and dismounting of the mounting bracket 16 to the counterpart at the measurement site without using any tools.

The temperature measuring sensor 23 may be an infrared temperature meter that is configured to detect the infrared radiation radiated from the moving tissue web 2, whereby the infrared radiation radiated from the moving tissue web 2 represents the temperature of the web 2. The infrared radiation of the moving tissue web 2 thus indicates the temperature of the moving tissue web 2 which, in turn, is directly proportional to the dryness of the moving tissue web 2 that is inversely proportional to the moisture of the moving tissue web 2.

The handhold element 22 provides a kind of controlling element by which the movement of the actuating member 21 and the temperature measuring sensor arranged to the actuating member 21 may be controlled by the hands of the person. The handhold element 22 may also be replaced for example with a motorized actuator to move the actuating member 21 back and forth.

The measuring device 15 further comprises at least one position measuring sensor 24 for measuring a position of the actuating member 21 relative to the mounting bracket 16, the position measuring sensor 24 determining the cross-directional position of the temperature measuring sensor 23 associating to the respective measurement result of the temperature of the moving tissue web 2 in the cross direction of the moving tissue web 2. The position measuring sensor 24 may for example be an optical sensor that is used to read a scale of length 27 arranged at a surface of the actuating member 21 as schematically shown in FIG. 5.

Figure 6:
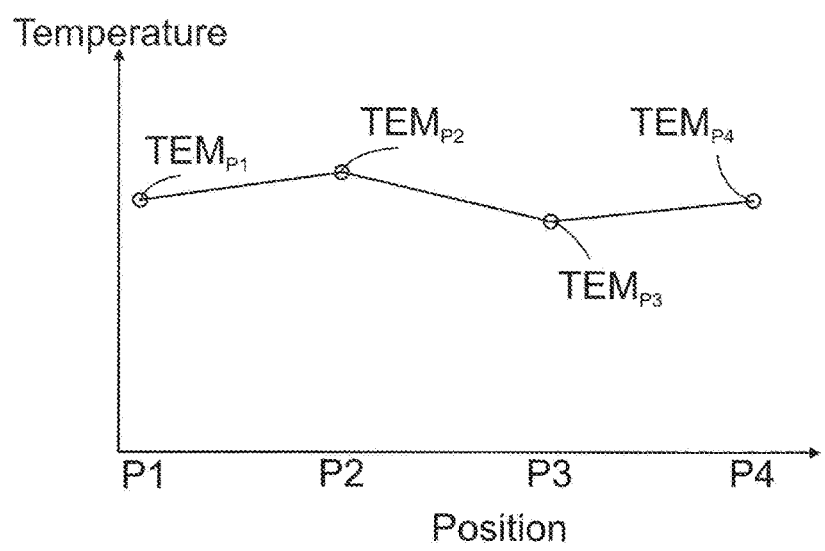
FIG. 6 shows schematically an example of a shape of a cross direction temperature profile of a moving tissue web.

The measuring device 15 further comprises at least one analysis device 25 configured to receive from the temperature measuring sensor 23 the measurement results of the temperature and to receive from the position measuring sensor 24 cross-directional positions of the temperature measuring sensor 23 corresponding to the above-mentioned temperature measurement results as measured by the temperature measuring sensor 23. By associating the temperature measurement results as measured by the temperature measuring sensor 23 with the respective cross-directional positions of the temperature measuring sensor 23 as indicated by the position measuring sensor 24 the cross-direction profile of the temperature of the moving tissue web 2 may be formed. FIG. 6 shows schematically an example of a possible shape of the cross direction temperature profile of the moving tissue web 2, wherein reference sign TEMP1 corresponds to the measured temperature of the moving tissue web 2 at the measurement position P1, TEMP2 corresponds to the measured temperature of the web 2 at the measurement position P2, TEMP3 corresponds to the measured temperature of the web 2 at the measurement position P3 and TEMP4 corresponds to the measured temperature of the web 2 at the measurement position P4.

At the beginning of the measurement operation the actuating member 21 is pulled backwards to such an extent that the temperature measuring sensor 23 at the second end 21" of the actuating member 21 is positioned at the front edge 2a of the moving tissue web 2 and the position measuring sensor 24 is initialized or adjusted to zero for starting the measurement. Thereafter the person operating the measuring device 15 pushes the actuating member 21 forward across the moving tissue web 2 towards the rear edge 2b of the moving tissue web 2, i.e. in the direction of the arrow indicated with reference sign M in FIGS. 4 and 5, until the temperature measuring sensor 23 has passed the rear edge 2b of the moving tissue web 2. At the same time when the temperature measuring sensor 23 travels over the moving tissue web 2 the temperature measuring sensor 23 measures at certain time periods the infrared radiation radiating from the moving tissue web 2, the amount of the infrared radiation representing the temperature of the moving tissue web 2. A measurement of the infrared radiation at a position of the moving tissue web 2 in the cross direction thereof provides a measurement result of the temperature of the moving tissue web 2 at the respective cross-directional position of the moving tissue web 2. At the same time the position measuring sensor 24 measures the position of the temperature measuring sensor 23 corresponding to the respective temperature measurement of the moving tissue web 2 in the cross direction of the web 2. As mentioned earlier the traversing movement of the sensor 23 cross-wise over the tissue web 2 can be performed automatically by an actuator such as a step motor.

The temperature measuring sensor 23 is configured to send the temperature measurement, referred to with reference sign TEM in FIG. 5, to the analysis device 25 over a data transfer connection. The position measuring sensor 24 is configured to send a respective measurement position of the temperature measuring sensor 23 in the cross direction of the moving tissue web 2, as measured by the position measuring sensor 24 and referred with reference sign POS in FIG. 5, to the analysis device 25 over another data transfer connection. The analysis device 25 receives and allocates the measured temperatures of the moving tissue web 2 with the respective measurement cross-directional positions of the temperature measuring device 23 for forming the cross-direction temperature profile of the moving tissue web 2. The analysis device 25 may comprise a necessary number of memory elements for storing the temperature measurement information and the position measurement information and at least one microprocessor or a similar processing element for executing a computer program product for formation of the cross directional temperature profile of the moving tissue web 2, as shown for example in FIGS. 2a, 2b and 6. The analysis device 25 may further comprise a display unit for displaying the measured temperature values and the temperature profile. The analysis device 25 may for example be a portable computer.

It should be noted that the actual number of the measurement positions or points in the cross direction of the moving tissue web 2 and their exact positions in the cross direction of the moving tissue web 2 may vary in many ways between different measurement procedures. They may depend for example on how fast the actuating member 21 and the temperature measuring sensor 23 arranged thereto is moved in the cross direction of the moving tissue web 2, the response time of the temperature measurement sensor 23, i.e. the time needed by the temperature measurement sensor 23 to complete the single temperature measurement of the moving tissue web 2, and a width of the moving tissue web 2. It is also possible to stop the movement of the temperature measurement sensor 23 at any desired position in the cross direction of the moving tissue web 2 so that a number of single measurement results of the temperature of the moving tissue web 2 at a desired cross directional position of the moving tissue web 2 are obtained. In this way it is also possible to determine a temperature profile of the moving tissue web 2 in the longitudinal direction thereof at any desired position in the cross direction of the moving tissue web 2.

Because the determined cross directional temperature profile of the moving tissue web 2 is directly proportional to the cross directional dryness profile of the moving tissue web 2, the shape of the cross directional temperature profile of the moving tissue web 2 indicates the shape of the cross directional dryness profile of the moving tissue web 2. Therefore the presentation of the shape of the cross directional temperature profile of the moving tissue web 2 presents in practice also the shape of the cross directional dryness profile of the moving tissue web 2 and no conversion of the shape of the cross directional temperature profile of the moving tissue web to the shape of the cross directional dryness profile of the moving tissue web by the analysis device 25 is necessarily needed. If it is preferred to present the shape of the cross directional moisture profile of the moving tissue web, it may be provided by an inverse of the shape of the cross directional temperature profile of the moving tissue web 2 as carried out by the analysis device 25.

Additionally the measuring device 15 may include a signal conversion device 26 allocated between the analysis device 25 and the temperature measuring sensor 23 and the position measuring sensor 24. The signal conversion device 26 may include a converter for providing possibly needed signal conversion between analogue and digital signal formats so as to provide a signal format suitable to be received by the analysis device or an accessory connected thereto. Instead of that or in addition to that the signal conversion device 26 may comprise an amplifier for amplifying the measuring signals received from the temperature measuring sensor 23 and the position measuring sensor 24. The signal conversion device 26 is shown schematically in FIG. 5 with a box drawn with a broken line.

The measuring device 15 disclosed provides a measuring device that may be moved or transferred from one measurement site in the tissue machine 1 to another measurement site and which measuring device 15 may be located in the tissue machine 1 at a desired location wherein a property of the moving tissue web 2 is intended to be temporarily measured. An introduction of the measuring device 15 for providing the measurement operation and a dismantlement of the measuring device 15 after carrying out of the measurement operation is easy. The measuring device 15 disclosed herein allows the measurement of the properties of the moving tissue web 2 in locations or places in the tissue machine 1 wherein it is very difficult or unsafe or unprofitable to organize the measurement operation in another way.

The measuring device 15 is especially suitable for determining the cross directional moisture profile of the moving tissue web after the nip 6 between the Yankee cylinder 3 and the counter roll 5 before the tissue web 2 enters to the influence area of the hood arranged next to the Yankee cylinder. With the measuring device disclosed there is no need to take physical samples of the tissue web 2 for determining the cross directional moisture profile of the moving tissue web 2, i.e. there is no need for any physical interaction with the moving tissue web 2. The measurement procedure provided by the measuring device 15 disclosed is thus safe for the personnel carrying out the measurement. Because there is no physical interaction with the moving tissue web 2 the production of the tissue web 2 is not affected at all whereby no production of the tissue web 2 is lost.

Figure 7:
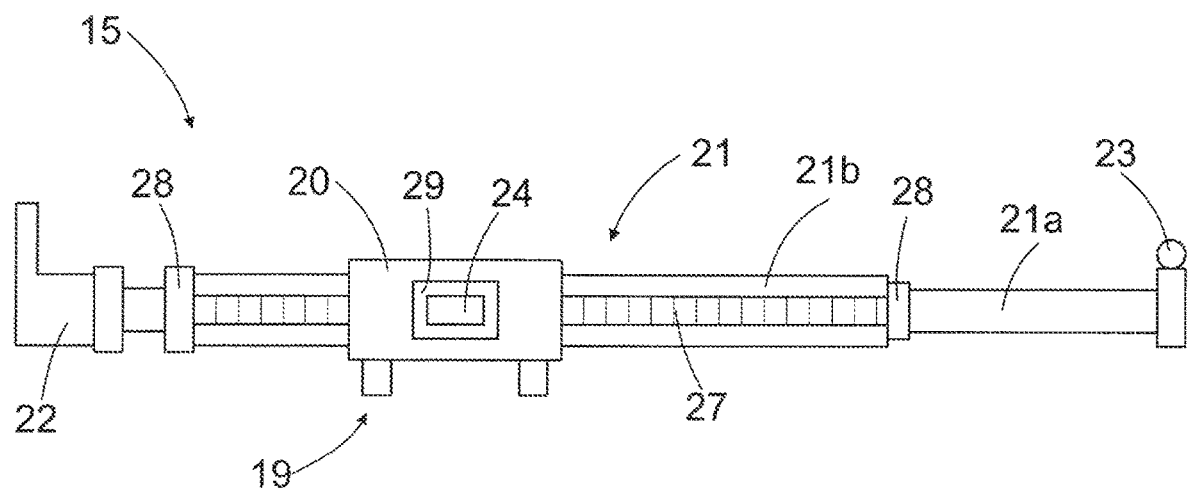
FIG. 7 shows schematically a side view of a part an alternative embodiment of a measuring device.

FIG. 7 shows schematically a side view of a part of another embodiment of a measuring device 15. The measuring device 15 of FIG. 7 may comprise all the parts already disclosed above but the mounting frame 17, mounting strap 18 and the signal conversion device 26 have been omitted in FIG. 7. The actuating member 21 in FIG. 7 comprises two coaxial actuating member parts, i.e. an inner actuating member part 21a having a form of an elongated rod or pipe and being arranged inside of an outer actuating member part 21b and supported thereto by ball bearing bushings 28, for example, the outer actuating member 21b having a form of an elongated tube or pipe. The handhold element 22 is arranged to the inner actuating member part 21 at the first end 21' of the actuating member 21 and the temperature measuring sensor 23 is arranged to the inner actuating member part 21 at the second end 21" of the inner actuating member part 21a. The supporter 20 is provided with a length scale measurement window 29 through which the length scale 27 is visible and at which the position measuring sensor 24 may also be arranged to measure absolute or relative positions along the length scale.

When the measuring device 15 of FIG. 7 is operated, the outer actuating member part 21b is pulled into a back position in the cross direction of the moving tissue web 2, i.e. to the left in FIG. 7, and locked at that position. The locking has not been disclosed in FIG. 7 for the sake of clarity, but it may be arranged for example between the outer actuating member part 21b and the supporter 20 in a manner evident for a person skilled in the art. Thereafter the inner actuating member part 21a is moved relative to the outer actuating member part 21b such that the temperature measuring sensor 23 is at the front edge 2a of the moving tissue web 2, and the inner actuating member part 21a is locked relative to the outer actuating member part 21b. The locking between the inner 21a and the outer 21b actuating member parts has not been disclosed in FIG. 7 for the sake of clarity but it may arranged by several ways evident for a person skilled in the art. When the inner 21a and the outer 21b actuating member parts have been locked to each other in a position wherein the temperature measuring sensor 23 is at the front edge 2a of the moving tissue web 2, the position measuring sensor 24 is initialized or adjusted to zero relative to the length scale 27 for starting the measurement.

For starting the actual measurement the locking of the outer actuating member part 21b is released or loosed whereby the outer actuating member part 21b and the inner actuating member part 21a and the temperature measuring sensor 23 arranged to the inner actuating member part 21a are able to move together with the outer actuating member part 21b in the cross direction of the moving tissue web 2. When the outer actuating member part 21b is moved in the cross direction of the moving tissue web 2, the inner actuating member part 21a and the temperature measuring sensor 23 arranged to the inner actuating member part 21a thus also moves together with the outer actuating member part 21b in the cross direction of the moving tissue web 2, whereby the temperature measurement sensor 23 measures the temperature of the moving tissue web 2 in a number of cross directional positions of the web 2 and the position measuring sensor 24 determines the cross directional measurement positions of the temperature measuring sensor 23 associating to the respective measurement results determined by the temperature measurement sensor 23. The operator of the measuring device 15 may also stop the movement of the outer actuating member part 21b so that the temperature measuring sensor 23 may stay at a desired position in the cross direction of the moving tissue web 2 for a longer time. That position information may be retrieved either by inspecting the length scale through the length scale measurement window 29 or on the basis of the position information provided by the position measuring sensor 24.

After the intended measurement procedure has been carried out, the inner 21a and the outer 21b actuating member parts are moved as far away from the moving tissue web 2 as possible in the cross direction of the moving tissue web 2 and locked in that position, and thereafter the measuring device 15 is dismantled from its fastening point or location.

It will be obvious to a person skilled in the art that, as the technology advances, the inventive concept can be implemented in various ways. The invention and its embodiments are not limited to the examples described above but may vary within the scope of the claims. Therefore, according to an embodiment the measuring device 15 may include more than one measuring sensor arranged to the actuating member 21 for measuring more than only one property of the moving tissue web 2 simultaneously. Furthermore, in the specification the measuring device is described in connection with a tissue machine, but naturally it is applicable in other fiber web machines intended for manufacturing lignocellulose-containing fiber webs, such as paper machines and board machines. Also, the property of the moving tissue web to be measured may be some other than the temperature of the web.

The invention claimed is:

1. A traversable measuring device for determining a cross direction profile of a property of a moving lignocellulose-containing fiber web in a fiber web machine, the measuring device comprising:
   a property measuring sensor movable in a cross direction of the moving fiber web and configured to determine a measurement result representing the property of the web at a plurality of cross directional measurement positions in response to a movement of the property measuring sensor in the cross direction of the moving fiber web;
   a position measuring sensor configured to determine the cross directional measurement position of the property measuring sensor associated with each determined measurement result;
   an analysis device for receiving the measurement results representing the property of the moving fiber web and the respective cross directional measurement positions and for associating the measurement results of the property of the moving fiber web with the respective cross directional measurement positions of the property measuring sensor for forming the cross direction profile of the property of the moving fiber web; and
   a mounting bracket that is detachably fixable without tools for fastening the measuring device at a measurement site in the fiber web machine, wherein the property measuring sensor and the position measuring sensor are supported with respect to the mounting bracket.

2. The device of claim 1 wherein the measuring device comprises an actuating member by which the property measuring sensor is connected to a controlling element and by which the movement of the actuating member and the property measuring sensor is controlled in the cross direction of the moving fiber web, and wherein the mounting bracket is configured to receive the actuating member such that the actuating member is movable relative to the mounting bracket as controlled by the controlling element.

3. The device of claim 2 wherein the mounting bracket comprises a mounting frame comprising the at least one magnetic part or portion for fastening the mounting frame to a counterpart for the measuring device at least by a magnetic force generating between the at least one magnetic part or portion of the mounting frame and the counterpart forming the fastening point for the mounting bracket, and a support stand that is fastened detachably to the mounting frame and comprises a supporter configured to receive the actuating member such that the actuating member is movable relative to the supporter as controlled by the controlling element.

4. The device of claim 1 wherein the mounting bracket comprises at least one magnetic part or portion for fastening the mounting bracket to a counterpart forming a fastening point for the mounting bracket at the measurement site at least by a magnetic force generating between the at least one magnetic part or portion of the mounting bracket and the counterpart forming the fastening point for the mounting bracket.

5. The device of claim 1 wherein the mounting bracket comprises at least one fastening strap for fastening the mounting bracket to a counterpart forming the fastening point for the mounting bracket at least by a clamping force generated by the at least one fastening strap between the mounting bracket and the counterpart forming the fastening point for the mounting bracket.

6. The device of claim 5 wherein the mounting bracket comprises a mounting frame and at least one fastening strap to be arranged around the counterpart for the measuring device and fastened to opposite sides of the mounting frame so as to fasten the mounting frame to the counterpart by the clamping force generated by the at least one fastening strap between the mounting frame and the counterpart, and a support stand that is fastened detachably to the mounting frame and comprises a supporter configured to receive the actuating member such that the actuating member is movable relative to the supporter as controlled by the controlling element.

7. The device of claim 1 wherein the mounting bracket has portions which fasten to a counter roll bearing housing of a counter roll which presses the moving fiber web against an outer surface of a Yankee cylinder in the fiber web machine, whereby the property of the moving fiber web is to be measured in a direction of motion of the fiber web at a location after the counter roll where the fiber web is supported against the Yankee cylinder.

8. The device of claim 7 wherein the analysis device is configured to convert a shape of the measured cross direction temperature profile of the moving fiber web to a shape of a cross direction profile of a property indicating a moisture profile of the moving fiber web on a basis of a correlation between the temperature of the moving fiber web and the property indicating the moisture of the moving fiber web.

9. The device of claim 1 wherein the property measuring sensor is a measuring sensor which measures a property which correlates a to a moisture content of the moving fiber web.

10. The device of claim 9 wherein the property measuring sensor is a temperature sensor.

11. The device of claim 10 wherein the property measuring sensor is an infrared temperature meter configured to measure infrared radiation radiated by the moving fiber web.

12. The device of claim 1 wherein the position measuring sensor is an optical encoder.

13. A method for determining a cross direction profile of a property of a moving lignocellulose-containing fiber web in a fiber web machine comprising a Yankee cylinder and a counter roll for pressing the moving fiber web against an outer surface of the Yankee cylinder, wherein a mounting bracket that is detachably fixable without tools is positioned at a measurement site in the fiber web machine, and a transversable measuring device is fastened to the mounting bracket, wherein the transversable measuring device comprises:
a property measuring sensor movable in a cross direction of the moving fiber web and configured to determine a measurement result representing the property of the web at a plurality of cross directional measurement positions in response to a movement of the property measuring sensor in the cross direction of the moving fiber web;
a position measuring sensor configured to determine the cross directional measurement position of the property measuring sensor associated with each determined measurement result; and
an analysis device for receiving the measurement results representing the property of the moving fiber web and the respective cross directional measurement positions and for associating the measurement results of the property of the moving fiber web with the respective cross directional measurement positions of the property measuring sensor for forming the cross direction profile of the property of the moving fiber web;
wherein the property measuring sensor and the position measuring sensor are supported with respect to the mounting bracket, wherein the method comprises the steps of:
determining a measurement result representing the property of the web at a plurality of cross directional measurement positions in a direction of motion of the web at a location after the counter roll wherein the web is supported against the Yankee cylinder;
determining a measurement position associated with each of the plurality of cross directional measurement results of the property of the moving fiber web in the cross direction of the web; and
associating the measurement results of the property of the moving fiber web with the respective cross directional measurement positions and forming a cross-direction profile of the property of the moving fiber web.

14. The method of claim 13 wherein the fiber web machine further comprises at least one hood positioned next to the Yankee cylinder and after the counter roll in the machine direction; and
wherein the cross-direction profile of the property of the moving fiber web is determined at a measurement site between the counter roll and the hood and closest to the counter roll in the direction of motion of the fiber web.

15. The method of claim 14 wherein the cross-direction profile of the property of the moving fiber web is a moisture profile of the moving fiber web.

16. The method of claim 14 wherein the cross-direction profile of the property of the moving fiber web is a temperature profile of the web.

17. The method of claim 13 wherein infrared radiation radiated by the moving fiber web is measured for determining a cross directional temperature profile of the web, and that the measured cross direction temperature profile of the moving fiber web is converted to a cross direction profile of a property indicating a moisture profile of the moving fiber web on a basis of a correlation between the temperature of the moving fiber web and the property indicating the moisture of the moving fiber web.

* * * * *